United States Patent [19]

Klintworth et al.

[11] Patent Number: 5,525,522
[45] Date of Patent: Jun. 11, 1996

[54] METHOD FOR FIXING A BIOLOGICAL PREPARATION

[75] Inventors: Rolf Klintworth, Delmenhorst; Jan P. van Aken; Udo Kristen, both of Hamburg, all of Germany

[73] Assignee: Daimler-Benz Aerospace AG, Munich, Germany

[21] Appl. No.: 359,613

[22] Filed: Dec. 20, 1994

[30] Foreign Application Priority Data

Dec. 20, 1993 [DE] Germany .................. 43 43 461.4

[51] Int. Cl.⁶ .................................. G01N 1/00
[52] U.S. Cl. .................. 436/174; 436/128; 436/130; 436/172; 436/175; 424/75; 422/40; 435/40.5; 435/40.52
[58] Field of Search .............. 436/63, 128, 130, 436/172, 174, 175, 800, 825; 424/3, 75; 422/40; 435/40.5, 40.51, 40.52

[56] References Cited

U.S. PATENT DOCUMENTS

| | | | |
|---|---|---|---|
| 3,862,300 | 1/1975 | Wertlake et al. | 435/40.52 |
| 3,997,656 | 12/1976 | Wertlake et al. | 435/40.52 |
| 4,404,181 | 9/1983 | Mauthner | 435/40.52 |
| 4,946,669 | 8/1990 | Siegfried et al. | 435/40.52 |
| 5,401,625 | 3/1995 | Robinson | 435/4 |
| 5,422,277 | 6/1995 | Connelly et al. | 436/10 |

OTHER PUBLICATIONS

Hayat, *Fixation for Electron Microscopy*, 1981, pp. 9–10, 39–41, 44–45, 58–59, 62–63, 129–130, 137–140, 314–319.
Gray, *The Encyclopedia of Microscopy & Microtechnique*, 1973, pp. 153–165.
Grundlagen der Histocheme (Basics of Histochemistry) by H. Luppa, Vieweg Verlag, Braunschweig 1978 section 1, pp. 42,43,52.

*Primary Examiner*—Jill Warden
*Assistant Examiner*—Maureen M. Wallenhorst
*Attorney, Agent, or Firm*—W. G. Fasse; W. F. Fasse

[57] ABSTRACT

Biological preparations or specimens are treated for a subsequent microscopic inspection. For this purpose it is necessary that the inner structure that is to be studied does not change prior to and during inspection. It is thus necessary to subject the specimens to a chemical and/or mechanical pretreatment for increasing the permeability of the specimen surface to a fixation substance in the form of an aqueous solution that contains an aldehyde fixation agent, preferably a highly volatile fixation agent or substance. The exposure of the specimens to the fixation substance takes place by immersion and/or spraying and/or fumigation. The fixation agent is preferably volatile and in the form of an aldehyde proportion of about 5% by volume or of an acrolein proportion of about 10% by volume.

16 Claims, No Drawings

METHOD FOR FIXING A BIOLOGICAL PREPARATION

CROSS-REFERENCE TO RELATED APPLICATION

The present application relates to our copending, commonly assigned application U.S. Ser. No.: 08/359,816, filed simultaneously herewith, and entitled APPARATUS FOR FIXING A BIOLOGICAL PREPARATION, Our Docket No.: 3115.

FIELD OF THE INVENTION

The invention relates to a method for fixing a biological preparation or specimen for a subsequent microscopic inspection. The preparations are particularly plant specimens that are prepared for the subsequent microscopic inspection by using an aldehyde containing fixation substance.

BACKGROUND INFORMATION

Biological preparations, for example in the form of plant specimens must be prepared before they can be inspected under a microscope, such as an electron microscope. The preparation requires subjecting the specimens to a fixation process so that the tissue will retain its structure without deterioration prior to and during the microscopic inspection. The fixation process uses a fixation substance such as an aldehyde that penetrates into the tissue of the specimen, thereby preventing a change in the specimen that could otherwise be caused by the subsequent embedding steps and by the vacuum prevailing in the specimen chamber of an electron microscope.

Conventional fixation substances include, among others, aldehyde, primarily glutaraldehyde, formaldehyde, or even the unsaturated aldehyde acrolein, whereby the fixation substances are frequently also used as mixtures of these formaldehydes.

Conventionally, fixation substances are used in the form of aqueous solutions for the so-called immersion fixation. Less frequently, fixation may also be accomplished by using these substances in the gas phase for performing a so-called fixation by fumigation.

A substantial problem has been encountered heretofore in conventional fixation processes with regard to the speed at which the fixation substance enters into the tissue and fixes the fine structure of the specimen prior to any possibility of a change in that fine tissue structure. Such changes must be avoided since they defeat the purpose of the microscopic inspection. Especially the preparation of plant specimens or rather their fixation poses two problems. On the one hand, above ground plant portions are enclosed by a substantially water impermeable outer skin, the so-called cuticula. On the other hand, air is present in the intercellular interstices in the leaves of plants, whereby the penetration of liquid, including fixation solutions into the leaf tissue is made more difficult.

In a book entitled "Basics of Histochemistry" (Grundlagen der Histochemie), by Hans Luppa, published by Vieweg Verlag Braunschweig, 1978, section 1, pages 42 and 43, a method has been described for fixing biologic preparations by using aldehyde fixation substances. This publication further describes on page 52 that trichloroacetic acid may be effective by hydrolysis on the heteropolar valence bindings to thereby loosen the hydration status and that trichloroacetic acid penetrates quickly into the tissue to thereby cause a type of preliminary fixation.

In connection with most of the conventionally used fixation methods, the plant specimens are first mechanically comminuted. Thereafter, different fixation sequential steps are employed, depending on the particular type of plant specimen. These conventional fixation steps require a relatively large volume throughput of fixation solution, the disposal of which subsequently causes a critical environmental problem. Further, conventional fixation methods require repeated manual intervention by the operator so that conventional methods are not suitable for an automatically performed fixation sequence. Such automatically performable sequence of fixation steps, however, is indispensable for experiments to be performed, particularly in a spacecraft in outer space or in areas that are difficult to access, for example, outside in the field.

OBJECTS OF THE INVENTION

In view of the above it is the aim of the invention to achieve the following objects singly or in combination:

- to provide a fixation method for the preparation of biological specimens, especially plant specimens, whereby for a subsequent microscopic inspection, a sequence of fixation steps are to be easily performed as an automatic fixation sequence;
- to minimize the volume of toxic or otherwise environmentally critical fixation substances to be used;
- to avoid the need for comminuting the biological specimens prior to fixation so that the specimens can be fixed as individual units, so to speak;
- to provide a fixation method which can employ a spraying fixation and/or fumigation fixation that in both instances employs aldehydes as a fixation substance; and
- the present method shall be suitable for use in outer space as well as on earth, particularly outdoors.

SUMMARY OF THE INVENTION

The invention has achieved the above objects by the combination of a preparation first step with a fixation second step. In the first step the permeability of the specimen surface is increased for better especially quicker, penetration of the fixation substance, such as an aqueous solution, for example in the form of a fog, and/or a volatilized fixation substance forming a fumigating agent. In both instances an aldehyde to which the specimen is exposed in the second step, for example by immersion, by spraying, and so forth.

Advantages of the invention are seen in that comminution of the specimens is no longer necessary so that the specimens can be subjected to the fixation as individual units. Further, the invention can use a spray fixation or a fumigation fixation either singly or in combination, using an aldehyde in both instances. Another substantial advantage is seen in that the present fixation process can be performed automatically so that it is particularly useful for application in a spacecraft in outer space. Nevertheless, the present method is equally suitable for use on earth in a laboratory as well as outside in the field.

DETAILED DESCRIPTION OF PREFERRED EXAMPLE EMBODIMENTS AND OF THE BEST MODE OF THE INVENTION

In one embodiment of the invention the fixation substance is a fixation mixture containing an aldehyde which is sprayed into a fixation chamber, whereby the fixation takes place on the one hand out of the gas or fog phase due to the evaporation of an easily volatile fixation agent forming a fine spray fog and on the other hand out of the liquid phase which forms a thin, yet closed film on the surface of the plant specimen. The fixation out of the liquid phase is additionally facilitated in that the plant surface and particularly the cuticula is mechanically and/or chemically pretreated to increase its permeability to the aqueous solution of the fixation substance.

In order to achieve fixation out of the gas phase, a preferred embodiment of the invention uses a fixation mixture containing an easily volatilizing fixation agent which contains either 5% by volume of formaldehyde or about 10% by volume of acrolein respectively mixed with about 2% by volume of glutaraldehyde. The fixation then takes place advantageously under the influence of light, especially daylight, and in a high relative humidity which is substantially water saturated. Under these fixation conditions, mechanically formed slots in the cuticula of the specimen are maximally open so that the penetration of the gaseous fixation agent into the plant interior is facilitated. The fixation out of the liquid phase is further enhanced by the addition of about 0.01% by volume of a detergent, for example "Triton X-100" added into the fixation mixture. This detergent increases the wettability of the plant specimen surface while, on the other hand having no adverse influence on the retaining or maintaining of the infrastructure (ultrastructure) of the specimen.

The preparation step or steps used according to the invention for increasing the permeability of the specimen surface for the fixation substance, take place chemically and/or mechanically. In both instances, the hydrophobic barrier of the cuticula is attacked by the preparation step or steps to such an extent that the sprayed fixation substance can penetrate into the plant interior sufficiently quickly, particularly into the leaf interior. The chemical pretreatment takes place with the aid of a trichloroacetic acid which increases the permeability of the cuticula for aqueous solutions of the fixation substance without damaging the cell structure below the cuticula. In this chemical pretreatment the permeability can be further improved by increasing the wettability of the plant surface by the addition of 0.01% by volume of a detergent such as "Triton X-100" to the trichloroacetic acid pretreatment solution.

The optimal conditions regarding the concentration of the trichloroacetic acid and regarding the duration of exposure of the specimen to the pretreatment solution are preferably determined in a preliminary experiment. The concentration of the pretreatment solution and duration of its application to the specimen depend on the required permeability of the specimen surface to the fixation substance applied in the second step. The permeability can be ascertained by using a fluorescent dye stuff, such as coriphosphine. For this purpose, the plant specimens that have first been chemically treated are rinsed with distilled water and incubated with the fluorescent dye stuff. After incubation the specimens are again rinsed and then checked under a microscope for the penetration depth of the fluorescent dye stuff. The penetration depth of the dye stuff into the interior of the plant can be estimated on the basis of the coloring of the outer cell layers, thereby establishing an index for the permeability of the cuticula achieved by the preliminary chemical treatment of the specimens.

Instead of the chemical pretreatment, or in addition thereto, a mechanical pretreatment of the plant specimens may be performed preferably with abrasive silicon carbide having a maximal grain size of $\leq 10$ µm. Such a silicon carbide powder is blown through a fine nozzle with air pressure onto the surface of the plant leaves, whereby the particles cause small mechanical lesions of the cuticula, thereby enabling the plant to permit a rapid penetration of the fixation mixture into the plant interior.

Two example embodiments or experiments according to the invention will now be described. Ten day old radish sprouts were used in both experiments. The specimens were chemically pretreated for the first experiment. The specimens were mechanically pretreated for the second experiment.

Referring to the first experiment, the specimens were introduced into an experimental chamber with a controlled environment in which the relative humidity was increased to a maximum. A pretreatment solution was freshly prepared. The pretreatment solution contained 0.5% by volume of trichloroacetic acid and 0.01% of the detergent "Triton X-100". A buffer in the form of 0.02M phosphate was added to the aqueous mixture having a pH value of 7.4. About 2 ml of this pretreatment solution was sprayed onto the plant specimens. After an incubation time of about 10 minutes, an aqueous fixation solution separately prepared, was sprayed onto the pretreated specimens in the experimenting chamber. The aqueous fixation solution contained 4 ml of a 2% glutaraldehyde or 5% formaldehyde. The 5% formaldehyde was freshly prepared from paraformaldehyde (polyoxymethylene). The solution contained 0.02M phosphate as a buffer to provide a pH value of 7.4. Following an incubation time of about 1 hour the temperature in the experimenting chamber was reduced to 4° C. and the high relative humidity was maintained. Thereafter, these specimens were further treated in accordance with the requirements for an inspection under an electron microscope. In the present experiment the further treatment was a second fixation by means of osmiumtetraoxide, whereupon the specimens could be examined under an electron microscope.

In the second experiment in which the specimens were mechanically pretreated, the relative humidity in the experimenting chamber was also raised to a maximum. A quantity of silicon carbide powder having a maximal grain size of about 10 µm was blown with air pressure through a fine nozzle, onto the plant surface. The quantity of silicon carbide powder was measured on the tip of a spatulum. The mechanically prepared specimen was exposed immediately to the same fixation aqueous solution as was used in the first experiment except that 0.01% (vol.) of "Triton X-100" was added as a detergent by spraying the detergent into the experimenting chamber. Then, a further treatment with osmiumtetroxide for a second fixation was performed and the so prepared specimen was suitable for examination under an electron microscope.

A further experiment was performed to ascertain the permeability achieved by the specimens subjected to the preliminary treatment. Different plant specimens were pretreated with different pretreatment solutions having different concentrations of trichloroacetic acid. The separate specimens were then rinsed twice in distilled water and then incubated for 15 minutes each in an 0.05% (vol.) aqueous dye stuff solution of coriphosphine. The incubated specimens were again rinsed by spraying and checked within 5 minutes in a microscope to ascertain the fluorescence and thus the penetration or permeability of the dye stuff into the interior of the plant specimen. The penetration depth of the dye provides an index for the permeability of the plant cuticula for the fixation substance.

Although the invention has been described with reference to specific example embodiments, it will be appreciated that it is intended to cover all modifications and equivalents within the scope of the appended claims.

What is claimed is:

1. A method for fixing a biological plant specimen having a specimen surface for a subsequent inspection in a microscope, comprising the following steps:
   (a) increasing the permeability of said specimen surface to the penetration of a fixation substance by a mechanical treatment applying an abrasive powder to said specimen, and
   (b) exposing said specimen surface to said fixation substance.

2. The method of claim 1, wherein said fixation substance is an aldehyde, and said exposing step comprises spraying said aldehyde as an aqueous fixation solution onto said specimen surfaces.

3. The method of claim 1, wherein said exposing step comprises fumigating said specimen surface with said fixation substance.

4. The method of claim 1, wherein said abrasive powder is silicon carbide powder.

5. The method of claim 1, wherein said mechanical treatment is performed by blasting said abrasive powder by pressurized air onto the specimen surface.

6. The method of claim 1, wherein said abrasive powder has a grain size of maximally about 10 μm.

7. The method of claim 1, wherein said fixation substance is an aqueous solution of aldehyde and a highly volatile additive.

8. The method of claim 1, wherein said fixation substance is an aqueous formaldehyde solution containing 5% formaldehyde by volume.

9. The method of claim 8, wherein said 5% formaldehyde contains 10% of acrolein by volume of said formaldehyde.

10. The method of claim 1, wherein said fixation substance is an aqueous aldehyde solution containing a detergent additive for improving the wettability of the specimen surface.

11. The method of claim 1, wherein said exposing of said specimen surface to said fixation substance takes place under the influence of light.

12. The method of claim 1, wherein said exposing of said specimen to said fixation substance is performed in a water saturated atmosphere.

13. The method of claim 1, further comprising adding to said fixation substance a buffer in the form of 0.02M phosphate.

14. The method of claim 1, wherein said step of exposing said specimen to said fixation substance is performed for about one hour.

15. The method of claim 1, further comprising, following said permeability increasing step, ascertaining with the aid of a fluorescent dye stuff the surface permeability of said specimen and then performing said exposing step on said specimen in accordance with said surface permeability.

16. The method of claim 1, wherein said fixation substance is an aqueous aldehyde solution containing 10% by volume of acrolein.

* * * * *